United States Patent

Wess

[11] Patent Number: 6,059,741
[45] Date of Patent: May 9, 2000

[54] DEVICE FOR TREATING CORPORAL TISSUE AND FOR CRUSHING CORPORAL CONCRETIONS

[75] Inventor: Othmar Wess, Lengwil-Oberhofen, Switzerland

[73] Assignee: Storz Medical AG, Switzerland

[21] Appl. No.: 09/043,662

[22] PCT Filed: Sep. 20, 1996

[86] PCT No.: PCT/DE96/01794

§ 371 Date: Mar. 19, 1998

§ 102(e) Date: Mar. 19, 1998

[87] PCT Pub. No.: WO97/10758

PCT Pub. Date: Mar. 27, 1997

[30] Foreign Application Priority Data

Sep. 20, 1995 [DE] Germany .......................... 195 34 809

[51] Int. Cl.[7] ................................................. A61B 17/22
[52] U.S. Cl. ...................................................... 601/4
[58] Field of Search .......................... 601/3, 4; 600/437, 600/438, 439, 459

[56] References Cited

U.S. PATENT DOCUMENTS

| | | |
|---|---|---|
| 5,060,634 | 10/1991 | Belikan et al. ............................. 601/4 |
| 5,144,953 | 9/1992 | Wurster et al. ............................. 601/4 |
| 5,305,731 | 4/1994 | Buchholtz .................................. 601/4 |
| 5,810,748 | 9/1998 | Ueberle ...................................... 601/4 |

Primary Examiner—Marvin M. Lateef
Assistant Examiner—Maulint Patel
Attorney, Agent, or Firm—St. Onge Steward Johnston & Reens LLC

[57] ABSTRACT

Disclosed is a device for treating corporal tissue and/or for crushing corporal concretions by means of acoustic energy, such as shock, pressure or ultrasonic waves using a sound generation unit which generates acoustic waves, if need be, a downstream bundling unit for the acoustic waves, and a transmission medium for said acoustic waves generated by the sound generating unit, which medium conducts the acoustic waves to the body.

The present invention is distinguished by the fact that the form of the interface and/or the conditions at the interface between the transmission medium and the body are set in such a manner that the transmission of the energy from the sound generating unit into the body occurs without major deviations from the desired propagation.

18 Claims, 2 Drawing Sheets

DEVICE FOR TREATING CORPORAL TISSUE AND FOR CRUSHING CORPORAL CONCRETIONS

DESCRIPTION

1. Technical Field

The present invention relates to a device for treating corporal tissue and/or for crushing corporal concretions by means of acoustic energy, by way of illustration by means, of shock, pressure or ultrasonic waves according to the generic part of claim 1.

2. State of the Art

A device on which the wording of the generic part of claim 1 is based is known from EP-A-0 369 177. This printed publication, to which including the state of the art of the Search Report cited therein reference is explicitly made with regard to the explanation of all details not mentioned or described closer herein, describes a device which, e.g. can be utilized as an extracorporal lithotriptor.

The known devices of this type are provided with a sound generating unit which generates a plane, a cylindrical, an approximately ball-shaped or an already focused wave field in a transmission medium. If the generated wave field does not have the desired "bundling" respectively focusing, a bundling unit for the acoustic waves is disposed downstream of the sound generating unit. The bundling unit may be a reflector with a, depending on the design of the sound generating unit, paraboloid or elliptical cross section, shock wave tube and/or an acoustic lens, etc.

In the known processes of extracorporally induced lithotripsy or ultrasonic thermotherapy, the sound generating unit and, if need be, the provided bundling unit are disposed outside the human body, i.e. extracorporally. Depending on the treatment procedure to be carried out, continuous, pulsed or repetitive acoustic wave fields (pressure, shock, pulsed or unpulsed ultrasonic fields) are generated outside the body, coupled into the body via a coupling-in surface and concentrated at a target site in the body.

In the present commercially available lithotriptors, the acoustic waves are generated in water and then are coupled into the body via a water cushion or also in an open water bath. For good coupling-in, water seems to have much to recommend it as the transmission medium, because with good approximation it can be assumed that the corporal tissue and water have similar acoustic impedance. In this way the acoustic energy is transmitted into the body without major reflection losses. Water also has much to recommend it because it is easy to handle. This is the reason that today all known lithotriptors and ultrasonic thermotherapy devices work with water as the transmission medium.

In doing so the following has been assumed:

The acoustic impedance Z is defined by the product of the density and the sound propagation velocity c. If the impedance Z of the transmission medium is the same as or at least is approximately the same as the impedance of the corporal tissue, low loss energy coupling-in is ensured. This goal is also achieved even if the values for the density and the sound velocity differ distinctly in the two media as long as only the product of the respective values of the two media are at least approximately the same.

DESCRIPTION OF THE INVENTION

The present invention is based on understanding the following:

For the therapeutic effect of pressure, shock or ultrasonic waves not only the amount of the coupled-in energy is of significance but rather the concentration of energy is important for the actual action area. The focal energy density that can be reached in the body is decisively influenced by whether the waves can propagate without hindrance or whether they are deflected from the intended propagation direction by obstacles, i.e. refracted, scattered or bent. The deviations from the desired propagation direction are so much larger the farther they occur before the zone of action.

Obstacles at which the deviation from straight propagation occurs are, e.g. interfaces of organs where refraction and reflection occur due to a change in the propagation velocity. By way of illustration, the ultrasonic wave propagation velocity in the kidneys or in the liver differs partly by more than 50 m/s from in water.

An element of the present invention is that it was understood that this effect is not to be ignored, e.g., in lithotripsy.

Notably, this effect results in a lateral extension of the focus zone respectively therapy zone which, depending on the patient and position of the stone, can be about ±5 mm. Extension of the focus zone of this size leads to a significant reduction of the energy density in the therapy focus. In this, as proven in comparison with laboratory tests, the desired therapeutic effect, in this case successful crushing, is distinctly reduced.

Although, these deviations can only be completely compensated by complicated matching of the individual anatomic and the propagation conditions, an element of the present invention is that it was understood that even the first interface between the medium in which the acoustic waves are generated and the corporal tissue decisively influences the obtainable energy density in the focus:

The entry surface of the acoustic waves, i.e. the patient's skin, therefore has special influence, because it is farthest from the focal zone inside the body, thus small deviations from the straight propagation on the way to the focal zone result in considerable lateral deviations. Moreover, the fatty tissue immediately adjacent to the skin has an acoustic wave propagation velocity that is distinctly different from that of water so that major refraction effects are to be anticipated at this interface:

The propagation velocity in fatty tissue is between 1350 and 1480 m/s, whereas in water at temperatures between approximately 20° C. and 50° C., it is between 1480 m/s and 1550 m/s.

Therefore, the object of the present invention is to increase the efficiency respectively the performance of therapy devices which operate with concentrated acoustic waves by minimizing the deviations of the straight or predetermined propagation of acoustic waves at the passage from the transmission medium into the body and thereby raising the energy density in the focus.

An invented solution to this object is described in claim 1. Further embodiments are the subject matter of claims 2 and the following claims.

An element of the present invention is that the form of the interface respectively the conditions at the interface between the transmission medium and the body is set in such a manner that the transmission of energy from the sound generating unit into the body occurs without major deviations from the desired propagation.

Setting the conditions at the interface may, by way of illustration occur, in that a material is employed for the transmission of acoustic waves that, with regard to refraction index or in other words the propagation velocity, is matched as closely as possible to the surface tissue layer of the human body, thus index matching is carried out:

While it can be assumed that the fatty tissue close to the surface has an acoustic wave propagation velocity of about 1350–1400 m/s, water at a temperature of 32° C. approximately 1520 m/s and at higher temperatures even higher values must be reckoned with. In addition the hitherto employed criteria of impedance adaptation should be met as good as possible in order to avoid unnecessary reflection losses. Above all, care must be taken that the refraction indices are as close as possible, i.e. that no refraction of the acoustic waves occurs at the passage into the body due to which the focus zone is widened laterally in comparison to the "regular" passage of the sound waves.

Media which fulfill the conditions of "index matching" in good approximation are, e.g., certain oils which are available with propagation velocities of, e.g., 1400 m/s. Paraffin oil to name an example. Depending on the area of application and the anatomical conditions, other oils, other fluids or even solid bodies may be employed, in particular as "adaptation layer". Mixtures of such types of materials may also be used. If a suspension is used, care must be taken that the suspended particles do not scatter the sound waves.

It is largely of no consequence if the acoustic waves are already generated in a medium with a matched refraction index or if only the layer of the transmission medium coming into contact with the patient's body is matched.

Also of little importance is if the transmission medium is in immediate contact with the body or if one or multiple interface layers, such as coupler cushions, intermediate sheeting or the like prevent direct contact. As long as these intermediate layers are relatively thin, no significant deflection from the straight propagation occurs even if the acoustic waves pass through these layers diagonally.

A further, alternative or additional, possible way to avoid undesirable deviations from the straight or predetermined propagation of acoustic waves is to form the geometry of the interface in such a manner that the deviations do not occur or only in a controlled manner:

This may, e.g., occur in a different manner than with presently commonly employed lithotriptors and devices for ultrasonic thermotherapy in that the coupling surface is altered in a controlled manner. For instance, pressing on correspondingly formed applicators generates plane, spherical or otherwise regularly formed interfaces, respectively formed in a controlled manner, whose effect on the propagation of the acoustic waves can be selectively taken into account. In this manner too, action zones with high energy density can be generated inside the body and undesired deviations from the ideal propagation can be largely avoided.

In any event, the present invention provides a device whose efficiency is raised compared to conventional therapy devices working with concentrated acoustic waves. This increase in efficiency is the result of the invented measures due to which the deviations from the refraction of the waves from the "ideal passage" when the acoustic waves pass from the transmission medium into the patient's body are minimized. In this manner, a smaller focus can be obtained and therefore an increased density in the area of action.

BRIEF DESCRIPTION OF THE DRAWING

The present invention is made more apparent in the following using a preferred embodiment with reference to the drawing showing in.

DESCRIPTION OF A PREFERRED EMBODIMENT

Figure 1:
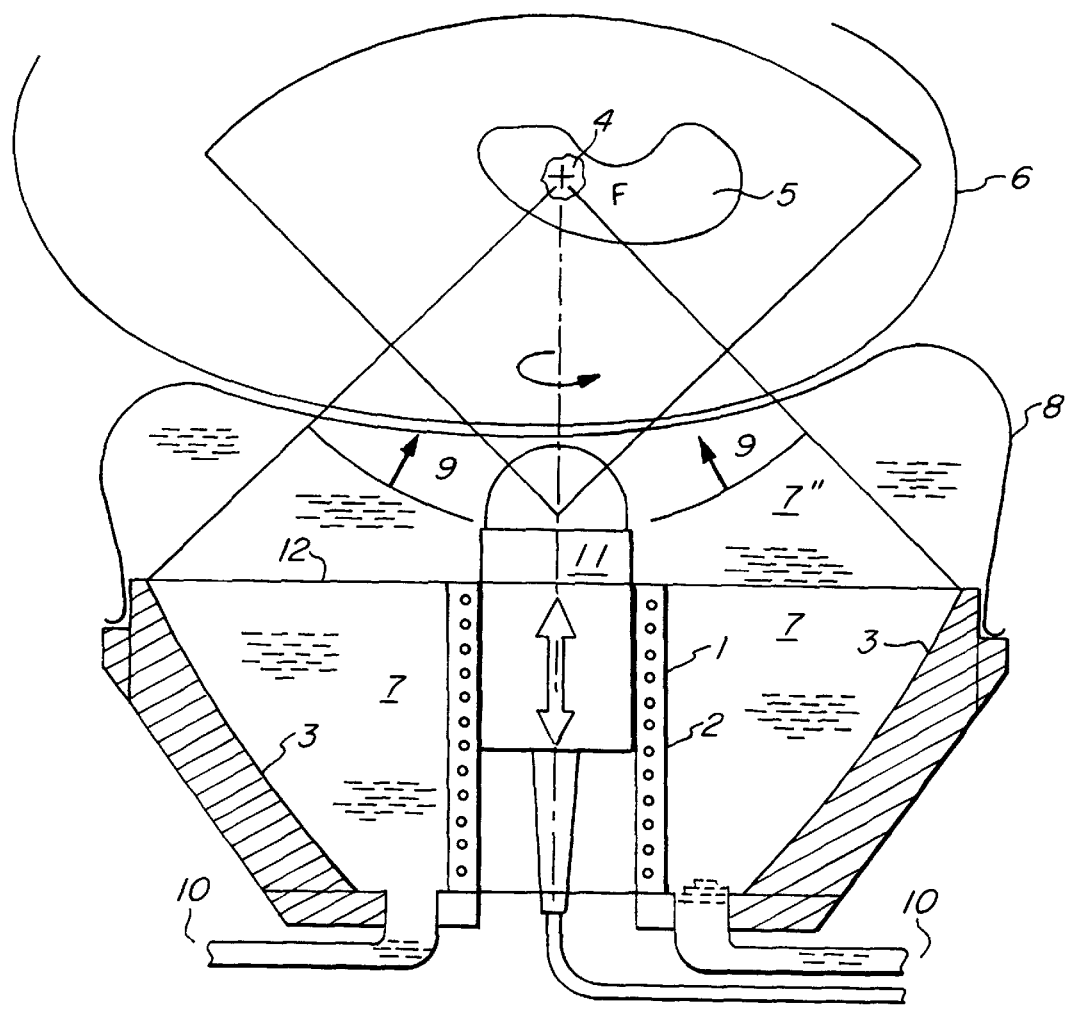
FIG. 1 a cross section of an invented apparatus

FIG. 1 shows, without any intention of limitation as an example, a device for treating corporal tissue and/or for crushing corporal concretions by means of shock waves as described in EP-A-0369 177. Of course, the present invention may also be applied to other devices, like those, by way of illustration, cited as the state of the art in the mentioned printed publication and which are provided with sound sources of other configurations.

The device shown in FIG. 1 is provided with a cylindrical coil 1 surrounded by a membrane 2 as the sound source respectively as the sound generating unit. The sound source radiates a cylindrical wave field which a reflector 3 "ideally focuses in a small area F". The reflector 3 has the form of a rotation paraboloid. At the "focal point" F is a stone 4 in a kidney 5. 6 stands for the outer contour of a human body.

In the shown preferred embodiment, the reflector 3 is sealed off by a sheeting respectively a membrane 8 yielding a closed chamber 7 which is filled with a transmission medium for the acoustic waves generated by the sound generating unit. The transmission medium conducts the acoustic waves 9 to the body 6. 10 stands for the lines with which the transmission medium can be pumped into chamber 7 respectively pumped out. 11 stands for an ultrasonic locating unit which is disposed inside the sound source and which can be moved in the direction of the axis.

To this extent the device shown in FIG. 1 is known from EP-A-0 369 177. In the known device, the transmission medium, which is located in chamber 7, is water which has a different refraction index than corporal tissue.

The same reference numbers are used in FIG. 2 as in FIG. 1 thereby obviating renewed introduction.

Figure 2A:
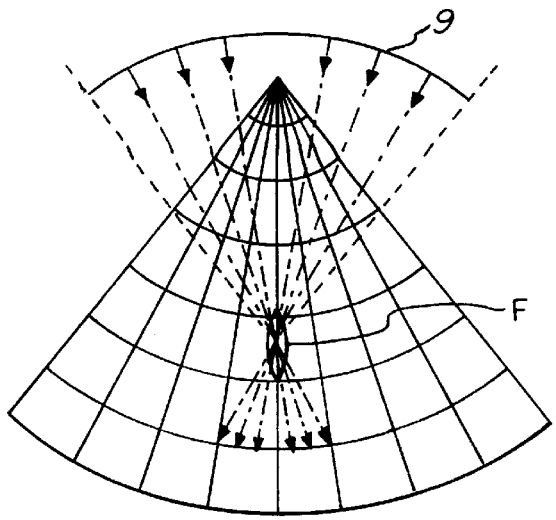
FIGS. 2a to 2c diagrammatic representations to explain the present invention.

FIG. 2a shows the conditions yielded by undisturbed wave propagation. The "straight" grid symbolizes the propagation of the ultrasonic waves. As FIG. 2a shows, the ultrasonic waves are focused in an area F with little lateral extension.

Figure 2B:
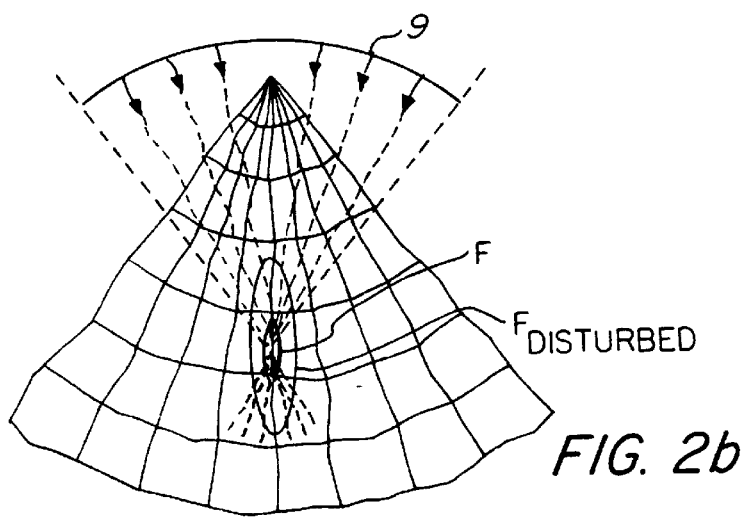

FIG. 2b shows the conditions yielded when wave propagation is disturbed due to the lack of index matching. The "wave-shaped" grid symbolizes the disturbed propagation of the ultrasonic waves. As FIG. 2b shows, the ultrasonic waves are focused in an area with interference with large lateral extension.

An element of the present invention is that this interference is at least reduced by the fact that the transmission medium in chamber 7 is matched with regard to the refraction index or, in other words, with its propagation velocity to the surface tissue layers of the body. For this purpose, a fluid, which has an acoustic wave propagation velocity in the range of 1350 to 1400 m/s, is selected as the transmission medium. A suited fluid, by way of illustration, is an oil and, in particular, a paraffin oil.

A second possibility is that the geometry of the coupling-in surface is designed in a controlled manner, e.g. is formed as a plane, spherical or aspherical surface whose influence on the propagation of the acoustic waves is known and is reflected in the determination of the focus position. For this purpose the sheeting respectively the membrane 8, which is used with coupler cushions of conventional devices, is replaced by an applicator which is pressed against the body with relatively high pressure in such a manner that a defined interface geometry between the human body 6 and the sound exit surface of the device is yielded. In the state of the art, however, an interface geometry is yielded that is dependent on the body contour.

Figure 2C:
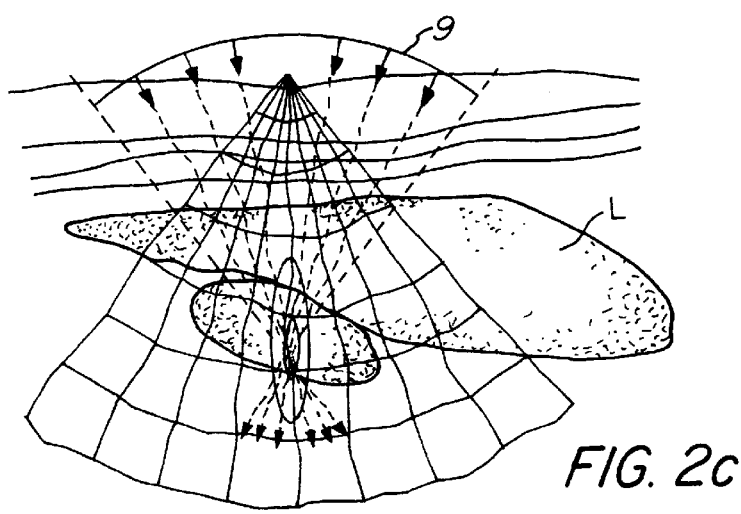

If non-rotationally symmetrical interfaces are employed, focus widening, like that yielded by scattering at the organs, such as by way of illustration the liver, is avoided. This is shown in a diagram in FIG. 2c depicting the actual conditions in the human body with the kidney and liver L.

As an alternative, chamber 7 can also, by way of illustration, be divided into two chambers at the line through a membrane with a defined form or selectively alterable form, of which the chamber surrounding the sound source 1 is filled with water and the chamber 7'' adjacent to the body 8 is filled with a fluid with a matching refraction index.

In any case, with the invented device for treating corporal tissue and for crushing corporal concretions high energy densities of pressure, shock or ultrasonic waves can be generated inside the body. Independent of the type of desired effect in the action zone of the device, with the aid of the invented device the effect of the applied acoustic energy in the defined action or focal zone is raised by improving the concentration of the energy on this zone compared to the conventional process, that more intensive action in the predetermined zone and simultaneously sparing the surrounding tissue is achieved.

What is claimed is:

1. A device for treating corporal tissue and/or for crushing corporal concretions by means of acoustic energy, using a sound generation unit which generates acoustic waves, and a sound generation unit which generates acoustic waves, and a transmission medium for the acoustic waves generated by the sound generating unit, characterized by the fact that an interface between said transmission medium and a body is set in such a manner that transmission of the energy from the sound generating unit into the body occurs without major deviations from a desired propagation, a refraction index of said transmission medium being matched with that of a surface of the corporal tissue of the body.

2. A device according to claim 1, characterized by the fact that a refraction index and a propagation velocity of said transmission medium is matched with that of a surface of the corporal tissue of the body.

3. A device according to claim 1, characterized by the fact that said transmission medium is provided with an acoustic wave propagation velocity in the range of 1350–1400 m/s.

4. A device according to claim 1, characterized by the fact that said transmission medium is an oil.

5. A device according to claim 4, characterized by the fact that said transmission medium is paraffin oil.

6. A device according to claim 1, characterized by the fact that said transmission medium comprises a closed container provided with a sound exit surface formed of sound-permeable material.

7. A device according to claim 6, characterized by the fact that said container is provided with internal and external chambers which are separated by a sound passage surface and wherein said external chamber is sealed off from the sound exit surface which forms the interface to the body.

8. A device according to claim 7, characterized by the fact that a propagation velocity of said transmission medium located in said external chamber matches that of the corporal tissue in the body.

9. A device according to claim 8, characterized by the fact that there is water in said internal chamber.

10. A device according to claim 7, characterized by the fact that the form of said sound passage surface can be altered.

11. A device according to claim 6, characterized by the fact that the sound exit surface is a membrane.

12. A device according to claim 6, characterized by the fact that an application which can be pressed against the body forms the sound exit surface.

13. A device according to claim 12, characterized by the fact that the the sound exit surface is matched to the body in a controlled manner.

14. A device according to claim 13, characterized by the fact that the sound exit surface is essentially a plane surface.

15. A device according to claim 13, characterized by the fact that the sound exit surface is essentially a spherical surface.

16. A device according to claim 13, characterized by the fact that the sound exit surface is essentially a spherical surface.

17. A device for treating corporal tissue and/or for crushing corporal concretions by means of acoustic energy, using a sound generation unit which generates acoustic waves, a transmission medium for the acoustic waves generated by the sound generating unit, characterized by the fact that an interface between said transmission medium and a body is set in such a manner that transmission of the energy from the sound generating unit into the body occurs without major deviations from a desired propagation, an impedance of said transmission medium matches that of the corporal tissue in the body.

18. A device according to claim 1, characterized by the fact that thin adaptation layers are provided.

* * * * *